(12) United States Patent
Ramsey

(10) Patent No.: US 7,571,657 B2
(45) Date of Patent: Aug. 11, 2009

(54) LIQUID SAMPLER

(75) Inventor: Charles A. Ramsey, Fort Collins, CO (US)

(73) Assignee: EnviroStat, Inc., Fort Collins, CO (US)

( * ) Notice: Subject to any disclaimer, the term of this patent is extended or adjusted under 35 U.S.C. 154(b) by 128 days.

(21) Appl. No.: 11/645,931

(22) Filed: Dec. 27, 2006

(65) Prior Publication Data
US 2008/0156115 A1  Jul. 3, 2008

(51) Int. Cl.
*G01N 1/22* (2006.01)
(52) U.S. Cl. .................................. 73/863.21
(58) Field of Classification Search ............. 73/863.21, 73/863.51, 863.52, 864; 422/101, 102
See application file for complete search history.

(56) References Cited

U.S. PATENT DOCUMENTS

| | | | | |
|---|---|---|---|---|
| 2,650,499 A | * | 9/1953 | Quist | 73/864.66 |
| 2,841,012 A | * | 7/1958 | Romer | 73/864.61 |
| 3,301,066 A | * | 1/1967 | Leonard et al. | 73/864.34 |
| 4,266,429 A | * | 5/1981 | Brovold | 73/864.63 |
| 5,693,894 A | | 12/1997 | Jobson | 73/863.03 |
| 6,168,758 B1 | * | 1/2001 | Forsberg et al. | 422/61 |

OTHER PUBLICATIONS

Web site cover page http://fisp.wes.army.mil/Catalog_Index.htm (3 pages)—Catalog Index and various product pages (23 pages) dated Dec. 20, 2006.

* cited by examiner

*Primary Examiner*—Hezron Williams
*Assistant Examiner*—Tamiko D Bellamy
(74) *Attorney, Agent, or Firm*—Craig Miles; CR Miles, P.C.

(57) ABSTRACT

A liquid sampler which provides a receptacle and a releasably sealable receptacle cover having at least two apertures each of which can be configured to adjust the flow rate of an amount of liquid into the liquid sampler upon submersion into a liquid.

18 Claims, 3 Drawing Sheets

US 7,571,657 B2

LIQUID SAMPLER

I. BACKGROUND

A liquid sampler which provides a receptacle and a releasably sealable receptacle cover having at least two apertures each of which can be configured to adjust the flow rate of an amount of liquid into the liquid sampler upon submersion into a liquid.

A conventional practice of sampling non-flowing surface water and most flowing surface water is to submerge an open ended receptacle or bottle into the surface water to collect a water sample. The receptacle or bottle containing the water sample can be sealed by with a cover or cap. The water sample obtained by collection with such a conventional sampler generates a water sample representative of the water at a single substantially fixed location over the duration of time required to fill the open ended receptacle. Because an open ended receptacle provides little or no restriction on the rate at which liquid flows into the receptacle or bottle, the duration of time over which the water sample is collected can be relatively short and the duration of time cannot be adjusted.

Another conventional practice of water sampling utilizes a closed receptacle having a tube which projects outwardly from the receptacle a distance sufficient to allow collection of an isokinetic sample in a flowing surface water, such as rivers or streams (for example see conventional samplers available from the United States Geological Survey). This conventional practice allows collection of a water sample which includes a representative sample of the suspended particulate in a sample of flowing surface water. While this type of conventional water sampler can provide an isokinetic sample of flowing surface water, collection of an isokinetic sample of a flowing water may not be necessary in the case of collecting samples of non-flowing surface water (for example from a lake or pond) or may not be desired even in the case of flowing surface water when a representative sample of the suspended particulate in the flowing surface water is not required or desirable. Additionally, these types of water samplers can be expensive relative to utilizing an open ended receptacle as above-described.

Despite advances in the art of water samplers and methods of water sampling, there remains a need for configurations of samplers which are relatively inexpensive and methods of sampling which allow flowing or non-flowing waters or other liquids to be sampled over greater durations of time than afforded by conventional open ended receptacles and which further provides sampling over a duration of time sufficient to collect water samples or other liquid samples as the liquid sampler travels a distance in the water or other liquid sample.

II. SUMMARY OF THE INVENTION

Accordingly, a broad object of the invention can be to provide a liquid sampler which provides a receptacle and a releasably sealable receptacle cover having at least two aperture elements each of which can be configured to adjust the flow rate of an amount of liquid into the liquid sampler upon submersion into a liquid.

A second broad object of the invention can be to provide a liquid sampler which provides at least two aperture elements configured to adjust flow rate of an amount of liquid into the liquid sampler allowing collection of liquid sample over a selected duration of time in the liquid.

A third broad object of the invention can be to provide a liquid sampler which provides at least two aperture elements configured to adjust flow rate of an amount of liquid into the liquid sampler allowing collection of liquid sample as the liquid sampler travels a selected distance in the liquid.

A fourth broad object of the invention can be to provide a liquid sampler which provides at least two aperture elements configured to adjust flow rate of an amount of liquid into the liquid sampler allowing collection of a liquid sample from a plurality of locations in a liquid or a plurality of liquids.

A fifth broad object of the invention can be to provide a liquid sampler which provides a receptacle and a releasably sealable receptacle cover having at least two aperture elements configured to adjust the flow rate of an amount of liquid into the liquid sampler upon submersion of the liquid sampler into the liquid which allows a liquid sample to be obtained as the liquid sampler travels a distance in the liquid over a selected duration of time.

A sixth broad object of the invention can be to provide methods of liquid sampling which generate a vertically integrated sample or a multi increment sample utilizing a sampler having a receptacle and a receptacle cover having at least two aperture elements configured to adjust the flow rate of an amount of liquid into the liquid sampler upon submersion of the liquid sampler into a liquid.

Naturally, further objects of the invention are disclosed throughout other areas of the specification, drawings, photographs, and claims.

III. A BRIEF DESCRIPTION OF THE DRAWINGS

IV. DETAILED DESCRIPTION OF THE PREFERRED EMBODIMENTS

Figure 1:
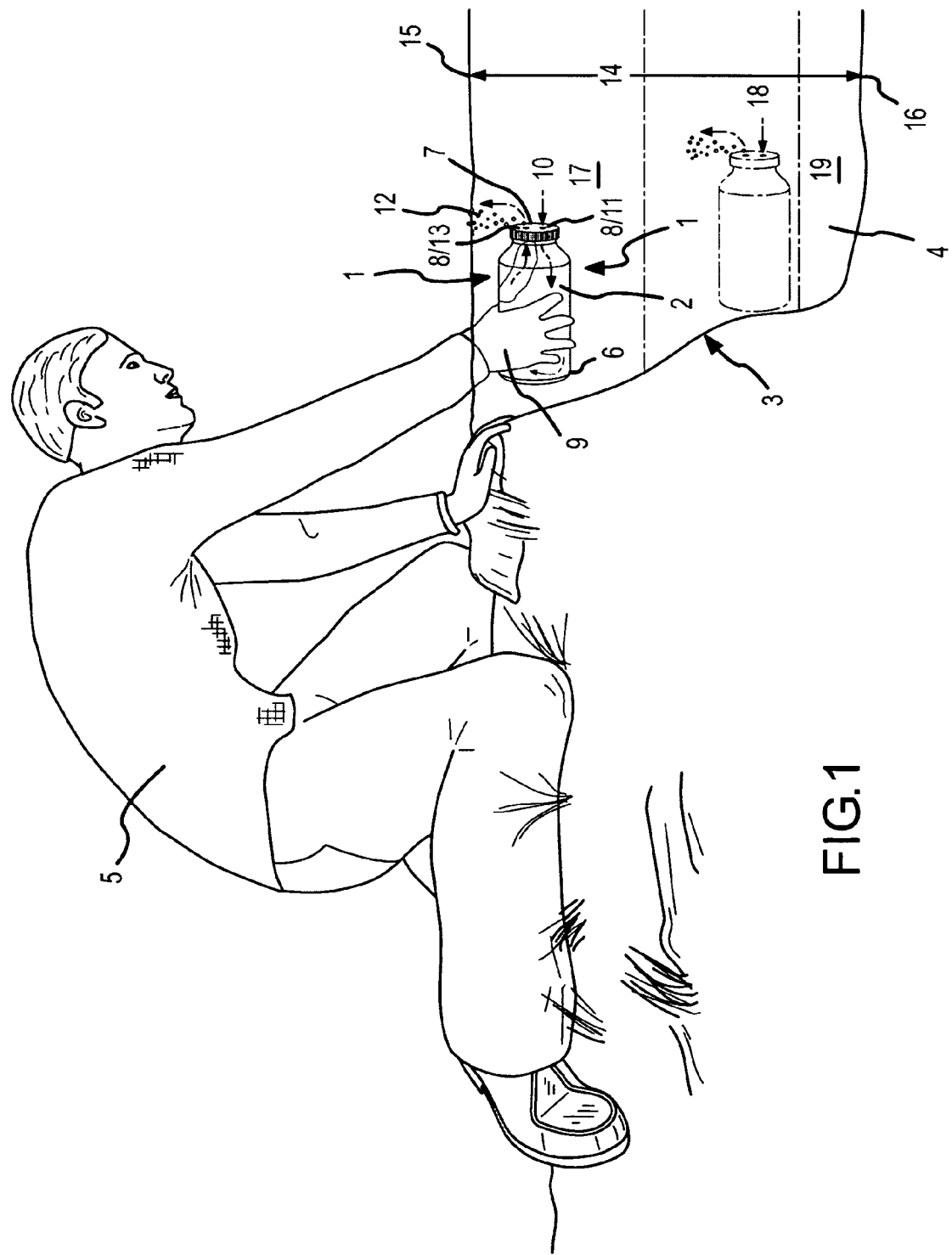
FIG. 1 illustrates an embodiment of a method of sampling a liquid with the inventive liquid sampler.

A liquid sampler which provides a receptacle and a releasably sealable receptacle cover having at least two aperture elements each of which can be configured to adjust the flow rate of an amount of liquid into the liquid sampler upon submersion into a liquid.

Now referring primarily to FIG. 1, which shows an embodiment of a method of utilizing the inventive liquid sampler (1)(hereinafter "liquid sampler") to collect a liquid sample (2) from a liquid (4) contained in a liquid source (3). The liquid source (3) can be any configuration of container whether manufactured or naturally occurring (such as a river bed, a lake bed, a tank, a drum, or the like) which can contain a liquid (4) whether a flowing liquid (such as a river, a stream, or the like) or a non-flowing liquid (such as a lake, a pond, a drum, a tank or the like). The liquid (4), can be an organic liquid (carbon containing compounds), a non-organic liquid (non-carbon containing compounds), a mixture or combination of one or more carbon containing compounds or non-carbon containing compounds or combination thereof, or a liquid which further includes particles whether biological particles such as animal or plant cells, algae, bacteria, viruses, or the like, or portions thereof, or non-biological particles such as suspended sediment, fines, tailings, or like. If the biological particles in the liquid sample (2) are to be assessed the liquid sampler (1) can be sterilized prior to collection of the liquid sample (2).

A liquid sample collector (5) can engage the liquid sampler (1) which includes a receptacle (6) to which the liquid sample collector (5) can releasably seal a receptacle cover (7) having at least two aperture elements (8). While FIG. 1 shows the liquid sample collector (5) as a person engaging the liquid sampler (1) in a hand (9), this example is not intended to be limiting with respect to the numerous and varied embodiments of the method of utilizing a liquid sampler (1) to collect a liquid sample (2) encompassed by the invention, and a liquid sample collector (5) can without limitation include any person, apparatus, device, or any part, portion, combination or permutation thereof, which can be configured to engage the liquid sampler (1) to allow a liquid sample (2) to be collected in the receptacle (6) as below described from a liquid (4) contained in a liquid source (3). As but one non-limiting example, the liquid sample collector (5) can be a person holding a pole or other extension device engaged to the liquid sampler (1).

To collect a liquid sample (2), the liquid sample collector (5) can submerge the liquid sampler (1) into the liquid (4) contained in the liquid source (3) with the at least two aperture elements (8) directionally located to allow an amount of liquid (10) to pass through a first aperture element (11) into the receptacle (6) and to allow an amount of gas (12) to pass through a second aperture element (13) to egress from the receptacle (6). Typically, the first aperture element (11) and the second aperture element (13) are aligned vertically or aligned with the force of gravity as shown in FIG. 1. During the period of time in which the liquid sample (2) is collected, the liquid sample collector (5) can maintain the liquid sampler (1) at a single location in the liquid (4), or the liquid sample collector (5) can generate vertical travel of the liquid sampler (1) over a vertical distance (14) in the liquid (4) between the liquid surface (15) and the bottom of the liquid source (16) or a portion of the distance (often referred to as a vertically integrated liquid sample), or the liquid sample collector (5) can obtain an amount of liquid (10) at a first location (17) in the liquid (4) and obtain a second amount of liquid (18) at a second location (19) in the liquid (4)(or a plurality of amounts of liquid from a corresponding plurality of locations in the liquid source)(often referred to as a multi increment sample) whether along a vertical travel path (vertically integrated multi increment sample) or in a horizontal travel path (horizontally integrated multi increment sample).

Figure 2:
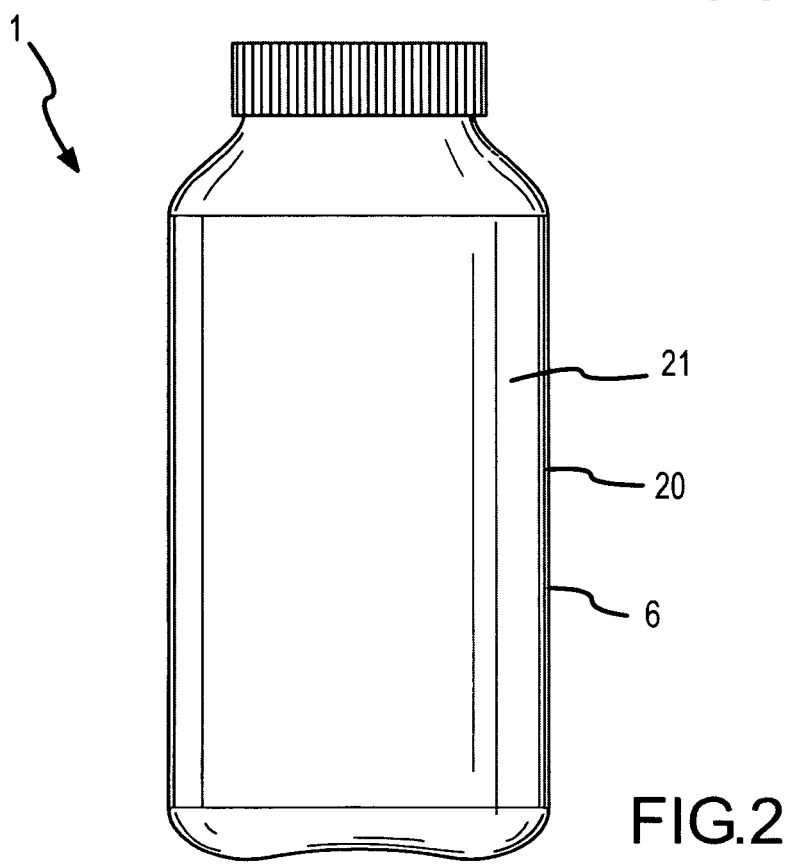
FIG. 2 is a top view of an embodiment of the inventive liquid sampler.
Figure 4:
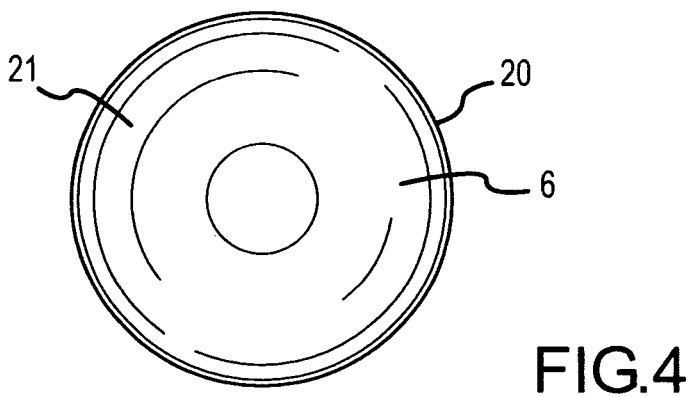
FIG. 4 is a bottom view of an embodiment of the inventive liquid sampler.
Figure 5:
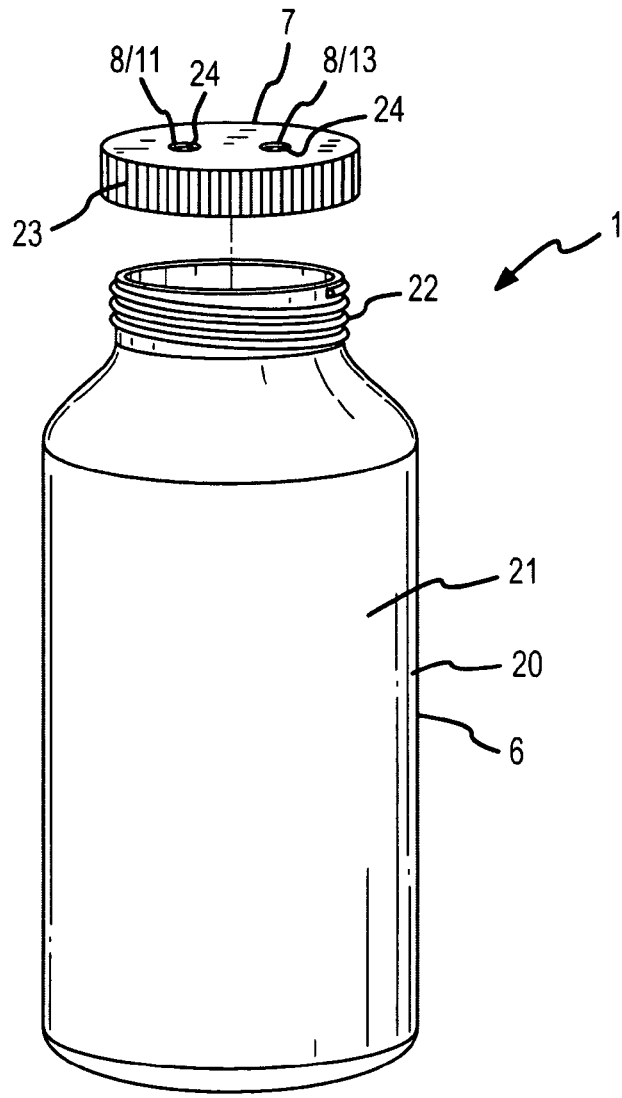
FIG. 5 is a perspective drawing which shows a receptacle cover which releasably seals a receptacle of an embodiment of the inventive liquid sampler.
Figure 6:
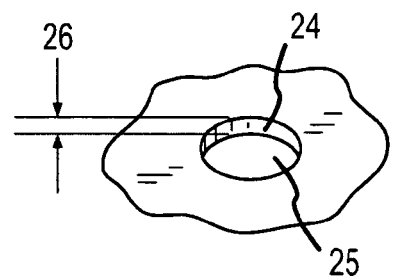
FIG. 6 is perspective view of an embodiment of an aperture element.

Now referring primarily to FIGS. 2, 4, and 5, the inventive liquid sampler (1) can provide a receptacle (6) having a receptacle wall (20) having a configuration which defines an amount of hollow space (21) inside the receptacle (6). While the embodiment of the receptacle (6) shown provides a generally cylindrical configuration, the invention is not so limited and the receptacle (6) can take any manner of constructional form or configuration which establishes hollow space (21) inside the receptacle (6) to receive the amount of liquid (10) or second amount of liquid (18)(or plurality of amounts of liquid) during collection of the liquid sample (2) as above-described and as but one additional example the receptacle (6) can be generally square in cross section.

Now referring primarily to FIGS. 2 and 5, the inventive liquid sampler (1) can further include a receptacle cover (7) which engages the receptacle (6) to enclose the amount of hollow space (21) inside the receptacle (6). As to certain embodiments of the inventive liquid sampler (1), the receptacle cover (7) releasably seals with the receptacle (6). The term "releasably seals" or "releasably sealable" generally encompasses any constructional form of the receptacle cover (7) and the receptacle (6) portions of which can be engaged to generate a seal between the receptacle cover (7) and the receptacle (6) sufficient to generally prevent transfer of the amount of liquid (10) or the liquid sample (2) between the engaged surfaces of the receptacle cover (7) and the receptacle (6) and which can be subsequently disengaged to break the seal between such portions of the receptacle (6) and the receptacle cover (7) to allow removal of the receptacle cover (7) from the receptacle (6). While FIG. 5 shows a constructional form of the receptacle (6) and the receptacle cover (7) which provides mated spiral threads (22)(23) which upon rotational engagement can generate the seal between portions of the receptacle (6) and the receptacle cover (7), the invention is not so limited, and various constructional forms of mated surfaces can be utilized which allow engagement and disengagement of portions of the receptacle (6) with the receptacle cover (7) to generate and release the seal above-described.

Figure 3:
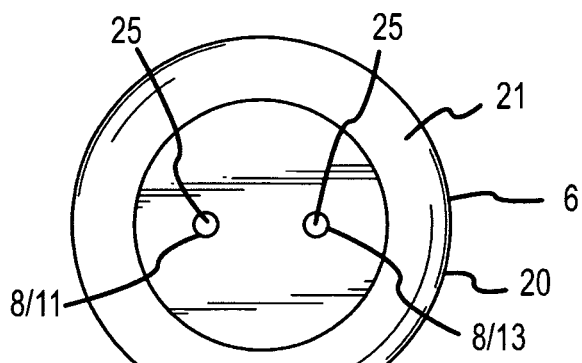
FIG. 3 is a side view of an embodiment of the inventive liquid sampler.
Figure 7:
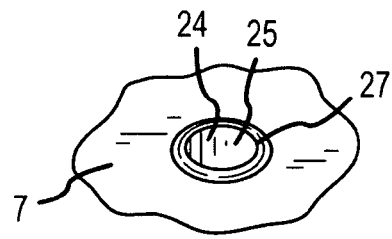
FIG. 7 is a perspective view of an embodiment of an aperture element having a thickened boundary.
Figure 8:
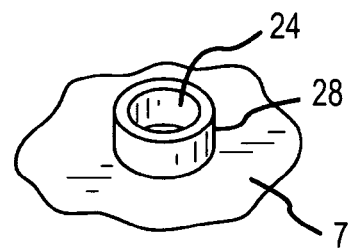
FIG. 8 is a perspective view of an embodiment of an aperture element having a tubular projection element.

Now referring primarily to FIGS. 1, 3 and 5, the inventive liquid sampler (1) can further include a first aperture element (11) and a second aperture element (13) disposed a distance apart on the receptacle cover (7). As shown by the embodiment of the liquid sampler (1) shown by the Figures, the first aperture element (11) and the second aperture element (13) can be located a distance apart on the bisection of a circularly configured receptacle cover (7); however, this example is not intended to limit the location of the first aperture element (11) or the second aperture element (13) to any particular location on the receptacle cover (7) or with respect to the relative location to one another. Rather, the first aperture element (11) and the second aperture element (13) can be located on the receptacle cover (7) at pair of locations which allow the first aperture element (11) and the second aperture element (13) to operate as below described in the collection of a liquid sample (2) of a liquid (4). The first aperture element (11) and the second aperture element (13) each have a boundary (24) which establishes a corresponding amount of open area (25) of the aperture element (11)(13). The example of the boundary (24) shown in FIGS. 3 and 5 comprises the thickness of the receptacle cover wall (26) although other configurations of the boundary (24) can include a thickened terminal edge (27) or a projection element (28) which extends a distance outward from the surface of the receptacle cover (7) at the boundary (24) as shown in FIGS. 7 and 8.

As shown in FIG. 1, the amount of open area (25) of the first aperture element (11) and the amount of open area (25) of said second aperture element (13) allow an amount of liquid (10) (or second amount of liquid or a plurality of amounts of liquid) to pass through the first aperture element (11) into the hollow space (21) inside the receptacle (6) while allowing an amount of gas (12) to pass through the second aperture element (13) to egress from the receptacle (6) upon submersion of the receptacle (6) sealed or releasably sealed to the receptacle cover (7) into the liquid (4). As to certain embodiments of the inventive liquid sampler (1), the boundary (24) of the first aperture element (11) and the boundary (24) of the second aperture element (13) can have substantially the same configuration, such as the embodiment shown in FIG. 3 each aperture element (11)(13) having generally circular configuration of substantially the same diameter (typically between one-sixteenth inch and one-half inch although other aperture diameters can be utilized depending upon the application) which affords each substantially the same amount of open area (25). However, it is not intended that the example shown limit the configuration of the boundary (24) of the first aperture element (11) or the boundary (24) of the second aperture element (13) to any particular configuration (for example the boundary can define a square, rectangle, oval or other geometry). Rather, the first aperture element (11) can have a boundary (24) which defines an open area (25) which can be of the same configuration or area, or of a different configuration or area, as to one receptacle cover (7). As but one example, the second aperture element (13) can have circular configuration of one-quarter inch in diameter through which an amount of gas (12) can egress from the receptacle (6) while the first aperture element (11) can have a circular configuration of one-half inch through which an amount of liquid (10) passes to enter the hollow space (21) inside the receptacle (6).

As to certain embodiments of the inventive liquid sampler (1), the first aperture element (11) and the second aperture element (13) can each have a boundary (24) adjusted in configuration to generate a particular flow rate of the amount of liquid (10) which passes into the hollow space (21) inside the receptacle (6) or to generate a particular flow rate of the amount of gas (12) which egresses from the receptacle (6). By generating a particular flow rate of the amount of liquid (10) or the amount of gas (12), or both the amount of liquid (10) and the amount of gas (12), the amount of liquid (10) included in the liquid sample (2) can be taken over a duration of time which corresponds to the established flow rate of the amount of liquid (10) and the volume of the liquid sample (2) collected, which for any particular liquid (4) can be established at about the same duration of time from liquid sample (2) to liquid sample (2) of the same volume collected. For example, the duration of time can be adjusted for a duration of time typically within a range of between 5 seconds and 300 seconds although a greater or lesser duration of time can be established depending on the particular application.

By decreasing the flow rate of the amount of liquid (10) passing into the hollow space (21) of the receptacle (6), the duration of time in which the liquid sample (2) can be collected can be increased. An increase in the duration of time over which the liquid sample (2) can be collected can establish a liquid sample (2) having liquid sample characteristics which more accurately represent the liquid (4) conditions at a particular location in the liquid source (3), or more accurately represent liquid (4) conditions over a selected duration of time in the liquid source (3), or allows the liquid sampler (1) to be located at more than one location in the liquid source (3) during collection of a single liquid sample (2), or allows the liquid sampler (1) to be located at a plurality of locations in the liquid (4) in the liquid source (3) during collection of the liquid sample (2), or allows an increased distance of vertical travel of the liquid sampler (1) through the liquid (4) in the liquid source (3) during collection of the liquid sample (2), or allows the liquid sampler (1) an increased distance of horizontal travel through the liquid (4) in the liquid source (3) during collection of the liquid sample (2), or each of the forgoing in various permutations and combinations.

As can be easily understood from the foregoing, the basic concepts of the present invention may be embodied in a variety of ways. The invention involves numerous and varied embodiments of an inventive liquid sampler and methods of producing and using such inventive liquid sampler.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "liquid sampler" should be understood to encompass disclosure of the act of "liquid sampling"—whether explicitly discussed or not—and, conversely, were there effectively disclosure of the act of "liquid sampling", such a disclosure should be understood to encompass disclosure of a "liquid sampler" and even a "means for liquid sampling." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the liquid samplers herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A water sampler, comprising:
   a) a receptacle; and
   b) a receptacle cover which releasably seals with said receptacle, wherein said receptacle cover has a first aperture element disposed a distance from a second aperture element, and wherein said first aperture element and said second aperture element each have a boundary which establishes an amount of open space which does not seal, and wherein said amount of open area of said first aperture element and said amount of open area of said second aperture element allow an amount of liquid to pass through said first aperture element into said receptacle while allowing an amount of gas to pass through said second aperture element to egress into a liquid from said receptacle upon submersion of said water sampler with said receptacle releasably sealed to said receptacle cover.

2. A water sampler as described in claim 1, wherein said amount of open area of said first aperture element is substantially equal to said amount of open area of said second aperture element.

3. A water sampler as described in claim 1, wherein said amount of open area of said first aperture element is different than said amount of open area of said second aperture element.

4. A water sampler as described in claim 2, wherein said amount of open area of said first aperture element and said amount of open area of said second aperture element is between about one-eighth square inch and about one-half square inch.

5. A water sampler as described in claim 4, wherein configuration of said boundary which establishes said amount of open area of said first aperture element and wherein configuration of said boundary which establishes said amount of open area of said second aperture element have substantially the same configuration.

6. A water sampler as described in claim 5, wherein configuration of said boundary which establishes said amount of open area of said first aperture element and wherein configuration of said boundary which establishes said amount of open area of said second aperture element have a circular configuration.

7. A water sampler as described in claim 6, wherein said circular configuration of said boundary which establishes said amount of open area of said first aperture element and wherein said circular configuration of said boundary which establishes said amount of open area of said second aperture element have a diameter of between about one eighth inch and about one half inch.

8. A water sampler as described in claim 7, wherein said releasably sealable receptacle cover includes a circular cover element, and wherein said first aperture element and said second aperture element have a location on the bisection of said circular cover element of said releasably sealable receptacle cover.

9. A water sampler as described in claim 8, further comprising a first spiral thread coupled to said receptacle and a second spiral thread coupled to said releasably sealable receptacle cover, where is first spiral thread and said second spiral thread rotatingly engage to releasably seal said receptacle cover to said receptacle.

10. A method of producing a liquid sampler, comprising the steps of:
   a. providing a receptacle;
   b. providing a receptacle cover which releasably seals to said receptacle; and
   c. establishing a first aperture element a distance from a second aperture element in said receptacle cover, wherein said first aperture element allows an amount of liquid to enter said receptacle, and wherein said second aperture element allows an amount of gas to egress from said receptacle into an amount of liquid upon submersion of said liquid sampler with said receptacle releasably sealed to said receptacle cover.

11. A method of producing a liquid sampler as described in claim 10, further comprising the step of adjusting a boundary of said first aperture element in said receptacle cover and adjusting a boundary of said second aperture element in said receptacle cover to adjust a liquid flow rate of said amount of liquid which enters said receptacle.

12. A method of producing a liquid sampler as described in claim 11, further comprising the step of adjusting said boundary of said first aperture element in said receptacle cover and adjusting said boundary of said second aperture element in said receptacle cover to adjust said liquid flow rate of said amount of liquid which enters said receptacle to allow said amount of liquid to be sampled over a vertical distance in said liquid over a duration of time.

13. A method of producing a liquid sampler as described in claim 12, further comprising the step of adjusting said liquid flow rate of said amount of liquid which enters said receptacle to allow said amount of liquid to be sampled over said vertical distance in said liquid of between about zero feet and about twenty feet.

14. A method of producing a liquid sampler as described in claim 13, further comprising the step of adjusting said liquid flow rate of said amount of liquid which enters said receptacle to allow said amount of liquid to be sampled over said duration of time in said liquid of between about 5 seconds and about 300 seconds.

15. A method of producing a liquid sampler as described in claim 14, further comprising the step of adjusting said boundary of said first aperture element in said receptacle cover and adjusting said boundary of said second aperture element in said receptacle cover to obtain a circular open area for each having a diameter of between about one-eighth inch and about one-half inch.

16. A method of producing a liquid sampler as described in claim 14, further comprising the step of establishing said first aperture element and said second aperture element a distance apart on the bisection of a circular cover element of said releasably sealable receptacle cover.

17. A method of sampling a liquid, comprising the steps of:
   a. submersing a receptacle releasably sealed to a receptacle cover which provides a first aperture element and a second aperture element in a liquid;
   b. establishing a flow of liquid through said first aperture element of said receptacle cover;
   c. establishing a flow of gas through said second aperture element of said receptacle cover, wherein a said first aperture element and said second aperture element have a boundary adjusted to allow said flow of liquid and said flow of gas to occur over a selected duration of time;

d. generating a distance of travel in said receptacle releasably sealed to said receptacle cover in said liquid as said liquid flows through said first aperture element of said receptacle cover;

e. sampling said liquid over said distance of travel in said receptacle relesably sealed to said receptacle cover.

18. A method of sampling a liquid as described in claim 17, further comprising the step of adjusting a boundary of said first aperture element and said second aperture element of said receptacle cover to allow said liquid sampled over said distance of travel to occur over a selected duration of time.

* * * * *